US00PP11514P

United States Patent [19]

Olesen et al.

[11] Patent Number: Plant 11,514

[45] Date of Patent: Sep. 19, 2000

[54] MINIATURE ROSE PLANT NAMED 'POULODY'.

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/138,033

[22] Filed: Aug. 18, 1998

[51] Int. Cl.[7] ..... A01H 5/00

[52] U.S. Cl. ..... Plt./116

[58] Field of Search ..... Plt./116, 122, 121

[56] References Cited

U.S. PATENT DOCUMENTS

P.P. 5,770 7/1986 de Ruiter ..... Plt./122

*Primary Examiner*—Howard J. Locker

[57] ABSTRACT

A new miniature pot rose plant which has abundant, non-fading, lavender-pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

The present invention constitutes a new and distinct variety of miniature rose plant which originated from a controlled crossing between an unnamed seedling and 'POULpol'. The two parents were crossed and the resulting seeds were planted in a controlled environment. The new variety is named 'POULody'.

The new rose may be distinguished from its seed parent, an unnamed seedling by the same inventors, by the following combination of characteristics:

1. 'POULody' has lavender-pink flowers, while the unnamed seedling has bluish-red flowers.

2. The parents of the unnamed seedling are 'Mainzer Fastnacht', a lavender hybrid tea and RUImired, U.S. Plant Pat. No. 5,770, a red miniature rose variety.

The new variety may be distinguished from its pollen parent, 'POULod' created by the same inventors, by the following combination of characteristics:

1. Flowers of 'POULody' have better lastingness.

2. 'POULody' has lavender-pink flowers while 'POULpol' has soft pink flowers.

3. 'POULodyl' has larger, but fewer flowers than 'POULpol'.

4. 'POULpol' is more compact.

The objective of the hybridization of this rose variety for commercial greenhouse culture was to create a new and distinct variety with unique qualities, such as:

1. Uniform and abundant flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULody' was selected by the inventors as a single plant from the progeny of the hybridization in April, 1995.

Asexual reproduction of 'POULody' by cuttings and traditional budding was first done by L. Pernille and Mogens N. Olesen in their nursery in Fredensborg, Denmark in September, 1995. This initial and other subsequent propagations conducted in controlled environments have demonstrated that the characteristics of 'POULody' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, stems, and a plant of 'POULody'. Specifically illustrated in SHEET 1:

1. Stem or entire plant showing branching and the attachment of leaves, buds, and peduncles;

2. Flower bud, partially opened bud, and open bloom;

3. Flower petals, detached;

4. Sepals, receptacle, and pedicel;

5. Flowering stem as well as a bare stem exhibiting thorns;

6. Leaves.

DETAILED DESCRIPTION OF THE VARIETY

The following is a detailed description of 'POULody', as observed in its growth in glasshouses in Fredensborg, Denmark and Half Moon Bay, Calif. and in field nursery in Jackson County, Ore. Color references are made using The Royal Horticultural Society (London, England) Colour Chart, 1995, except where common terms of color are used.

For a comparison, the nearest existing rose variety is 'POULprima', a patented variety by the same inventors described and illustrated in U.S. Plant Pat. No. 9,482 and issued on Mar. 26, 1996. Chart 1 details several physical characteristics of 'POULody' and 'POULprima'.

CHART 1

| | 'POULody' | 'POULprima' |
|---|---|---|
| Petal count | 50–60 petals | 30–35 petals |
| Bud color at ¼ open | Red-Purple Group 57B–57C | Red-Purple Group 61C |
| Color of upper surface of flower | Red-Purple Group 57B–57C | Red-Purple Group 61C |

-continued

CHART 1

| | 'POULody' | 'POULprima' |
|---|---|---|
| petal on an open flower | | |
| Basal petal spot | Outer petals: Greed-Yellow Group 1D<br>Inner petals: Green-Yellow Group 1D | Outer petals: Yellow Group 4C<br>Inner petals: Yellow Group 4A |

Parents: Unnamed seedling×'POULpol'.
Classification:
*Botanical.*—*Rosa hybrida*.
*Commercial.*—Miniature.

FLOWER AND FLOWER BUD

Blooming habit: Recurrent.
Flower bud:
*Size.*—Upon opening, 20 mm in length from base of receptacle to flower tip.
*Bud form.*—Ovoid.
*Bud color.*—As sepals unfold, Red-Purple Group 57A. Red-Purple Group 57B–57C at ¼ opening.
*Sepals.*—Green Group 143B. Weak foliaceous appendages on three of the five sepals. Exterior surfaces of the sepals moderately pubescent. Stipitate glands present.
*Peduncle.*—Surface: Grandular. With a moderate number of stipitate glands. Length: 40–60 mm average length. Color: Green Group 143B. Strength: Erect.
*Receptacle.*—Surface: Glandular. Shape: Broadly urn-shaped. Size: Medium. 6 mm tall×8 mm wide. Color: Green Group 143B.
*Borne.*—Generally with 1–3 buds per flowering stem.
Flower bloom:
*Size.*—Medium for a 13 cm pot rose. Average flower diameter is 45 mm when open.
*Form.*—Shape of flower when viewed from the side: Upon opening, upper part: Flat to cupped. Upon opening, lower part: Flat. Open flower, upper part: Flat to cupped. Open flower, lower part: Flat.
*Petalage.*—Double. Average range: 50–60 under normal conditions.
*Color.*—Upon opening, upper surface of the petals is Red-Purple Group 57A. Upon opening, the reverse surface is Red-Purple Group 57B–57C. After opening, the upper surface of the outermost petals is Red-Purple Group 57B. After opening, the upper surface of the innermost petals is Red-Purple Group 57C. After opening, the reverse surface is Red-Purple Group 57C. Upon opening, a petal spot, Green-Yellow Group 1D exists on the inner and outer sides of the bases of the petals. After opening, the petal spot is Green-Yellow Group 1D on the inner and outer bases of the petals.
*General tonality.*—No change in the general tonality at the end of 3–5 days. At the end of the 5th day, there is a slight change to Red-Purple Group 57D.
Petals:
*Petal reflex.*—Petals reflex backwards only slightly.
*Petal edge.*—With point at the center.
*Petaloids.*—Limited. Quantity: 1–5.

*Fragrance.*—Absent or very weak.
*Duration.*—As a pot plant, flowers last from 12 to 15 days. As a cut flower 8 to 10 days.
*Texture.*—Average.
*Shape.*—Rounded.
*Form.*—Reflexed slightly.
*Arrangement.*—Imbricated.
Reproductive organs:
*Pollen.*—Color: Prior to flower opening: Yellow Group 13B. On an open flower: Yellow-Orange Group 22A. Abundance: Average.
*Anthers.*—Size: Medium. Color: Yellow Group 13B. Abundance: Average.
*Filaments.*—Color: Yellow-Green Group 149D.
*Stigmas.*—Superior in location to anthers. Color: Yellow-Green Group 154D.
*Styles.*—Color: Yellow-Green Group 149D.

PLANT

Plant growth: Vigorous, compact, upright to bushy. When grown as a 13 cm pot plant, the average height of the plant itself is 20 to 22 cm and the average width is 23 to 25 cm. When grown as a nursery plant on its own roots the average plant height is 30–40 cm and the average plant width is 28–35 cm.
Stems:
*Color.*—Young wood: Green Group 138A. Older wood: Green Group 138A.
*Thorns.*—Incidence: Moderate. Size: Average length: 5 mm–6 mm. Color: Greyed-Green Group 193D. Shape: Linear.
*Bark.*—Young wood: Smooth. Older wood: smooth.
Plant foliage: Normal number of leaflets on normal leaves in middle of the stem: 5 leaflets.
*Leaf size.*—Medium. 85 mm (1)×55–60 (w) mm.
*Abundance.*—Moderately abundant.
*Color.*—Upper Leaf Surface: Green Group 137A. Lower Leaf Surface: Green Group 138B-138C. Juvenile foliage: Upper leaf surface: Green Group 137B with slight intonations of Greyed-Red Group 181A on margins. Lower leaf surface: Green Group 138B–138C with slight intonations of Greyed-Red Group 181A on margins and undersurface and petiole rachis.
Plant leaves and leaflets:
*Stipules.*—Present. Stipitate glands on margins. Size: 8 mm–10 mm. Color: Green Group 137B.
*Petiole.*—Length: 18 mm–22 mm. Color: Green Group 137B. Underneath: With fine prickles.
*Rachis.*—A few marginal stipitate glands. Color: Green Group 138A. Prickles: Underneath.
*Leaflet edge.*—Finely serrated.
*Shape.*—Leaflets are: Ovate.
*Other.*—Average thickness.
Disease resistance: Above average resistance to mildew and Botrytis under normal growing conditions in Half Moon Bay, Calif. and Fredensborg, Denmark.
We claim:

1. A new and distinct variety of rose plant of the miniature class, substantially as herein illustrated and described as a distinct and novel rose variety due to its abundant, lavender-pink flowers, vigorous and compact growth, year round flowering under glasshouse conditions, suitability for production from softwood cuttings in pots, and durable flowers and foliage which make the variety suitable for distribution in the floral industry.

* * * * *

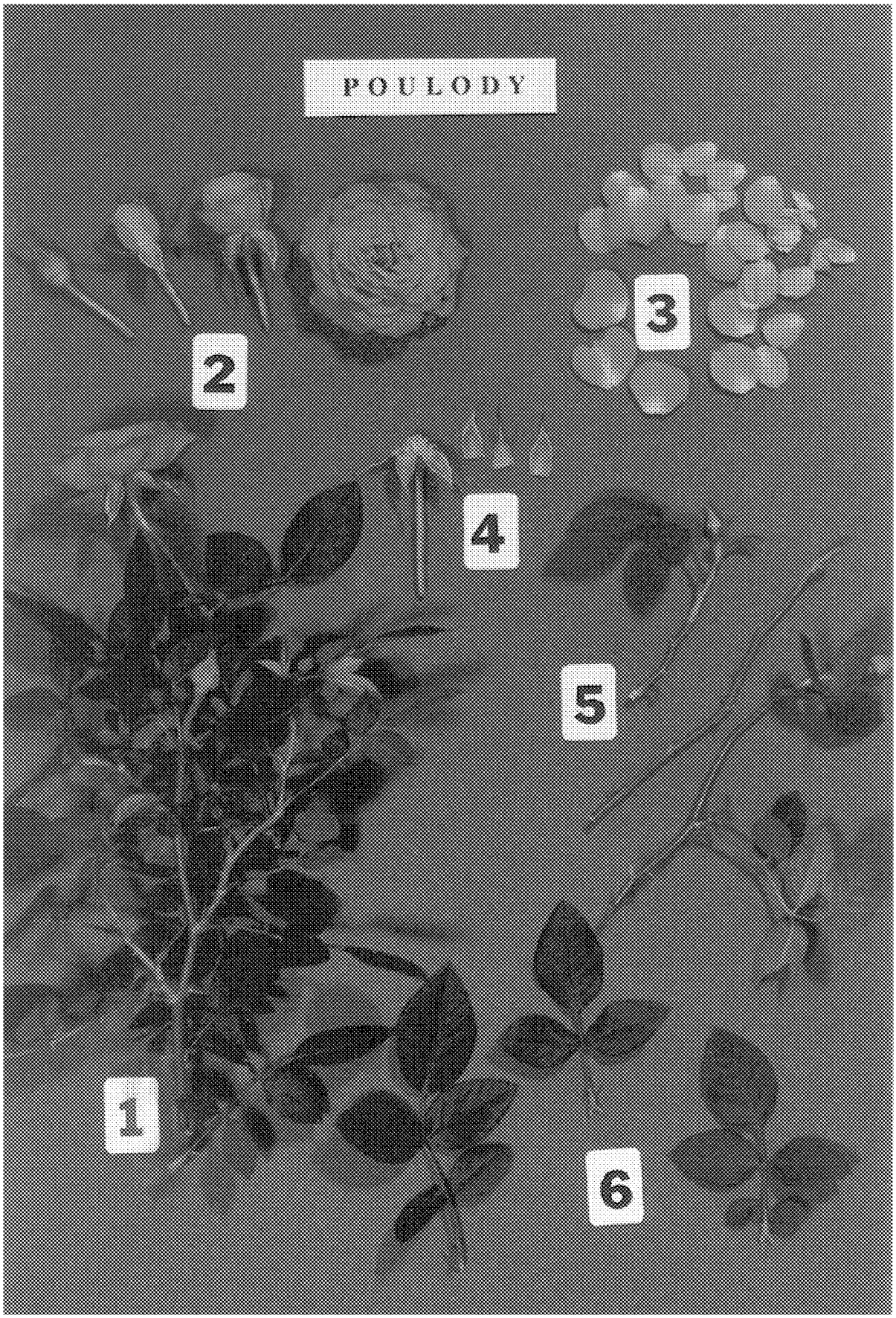
POULODY
1
2
3
4
5
6